United States Patent
Oakes et al.

(10) Patent No.: US 11,032,714 B2
(45) Date of Patent: Jun. 8, 2021

(54) COMMUNICATIONS PROTOCOL FOR AN ELECTRONIC SYSTEM

(71) Applicant: ViCentra B.V., Utrecht (NL)

(72) Inventors: Tim Oakes, Swansea (GB); Joseph Cefai, Swansea (GB)

(73) Assignee: ViCentra B.V., Utrecht (NL)

( * ) Notice: Subject to any disclaimer, the term of this patent is extended or adjusted under 35 U.S.C. 154(b) by 77 days.

(21) Appl. No.: 16/092,621

(22) PCT Filed: Apr. 20, 2017

(86) PCT No.: PCT/EP2017/059330
§ 371 (c)(1),
(2) Date: Oct. 10, 2018

(87) PCT Pub. No.: WO2017/190958
PCT Pub. Date: Nov. 9, 2017

(65) Prior Publication Data
US 2019/0124503 A1    Apr. 25, 2019

(30) Foreign Application Priority Data
May 6, 2016   (GB) .................................... 1607973

(51) Int. Cl.
*G06F 21/44*    (2013.01)
*H04W 12/55*    (2021.01)
(Continued)

(52) U.S. Cl.
CPC ........ *H04W 12/55* (2021.01); *A61M 5/14244* (2013.01); *G06F 21/44* (2013.01);
(Continued)

(58) Field of Classification Search
CPC .............................. G06F 21/44; H04L 63/0876
See application file for complete search history.

(56) References Cited

U.S. PATENT DOCUMENTS

| 6,544,228 B1 | 4/2003 | Heitmeier | |
| 2006/0031378 A1* | 2/2006 | Vallapureddy | ..... A61N 1/37288 709/208 |

(Continued)

FOREIGN PATENT DOCUMENTS

| CN | 103890768 A | 6/2014 |
| CN | 204910157 U | 12/2015 |

(Continued)

OTHER PUBLICATIONS

International Search Report and Written Opinion for International Application No. PCT/EP2017/059330, dated Jun. 22, 2017, 9 pages.

(Continued)

*Primary Examiner* — David J Pearson
(74) *Attorney, Agent, or Firm* — Armstrong Teasdale LLP

(57) ABSTRACT

The present invention proposes assigning a common system identification code to each of a control unit and a plurality of controllable slave units, storing that system identification code in a user-inaccessible memory of those units, and allowing pairing between the control unit and each of the slave units only if the system identification code of the control unit matches that of the respective slave unit. Thus a slave unit can only act upon a control signal if the control signal comes from the control master unit which shares the system identification code, i.e. is verifiably from the same family. This ensures that a slave unit only acts on instructions which come from a specified control unit, so providing security to the user. It is therefore impossible for a slave unit to act on instructions from any device other than the control master unit with which it shares a system identification code, which may be alternatively referred to as a family identification code or family ID.

17 Claims, 5 Drawing Sheets

(51) Int. Cl.
  *G08C 17/02* (2006.01)
  *H04W 84/20* (2009.01)
  *H04W 12/48* (2021.01)
  *A61M 5/142* (2006.01)

(52) U.S. Cl.
  CPC ............ *G08C 17/02* (2013.01); *H04W 12/48* (2021.01); *H04W 84/20* (2013.01); *G08C 2201/20* (2013.01); *G08C 2201/60* (2013.01)

(56) References Cited

U.S. PATENT DOCUMENTS

| | | | |
|---|---|---|---|
| 2006/0046654 A1 | 3/2006 | Shiozawa | |
| 2007/0249286 A1* | 10/2007 | Ma | H04L 63/18 455/41.3 |
| 2008/0285626 A1* | 11/2008 | Claus | H04W 12/06 375/133 |
| 2009/0195407 A1 | 8/2009 | Nakano et al. | |
| 2009/0232041 A1* | 9/2009 | Smith | H04W 12/04033 370/312 |
| 2010/0115279 A1* | 5/2010 | Frikart | G16H 40/63 713/171 |
| 2010/0318578 A1* | 12/2010 | Treu | G16H 40/67 707/802 |
| 2011/0267170 A1 | 11/2011 | Huang | |
| 2011/0320535 A1* | 12/2011 | Donaldson | H04W 12/003 709/204 |
| 2012/0093315 A1* | 4/2012 | Nierzwick | G16H 40/63 380/270 |
| 2013/0078912 A1 | 3/2013 | San Vicente et al. | |
| 2013/0205032 A1* | 8/2013 | Polefko | H04L 63/0876 709/227 |
| 2015/0207626 A1* | 7/2015 | Neftel | H04W 12/003 713/168 |
| 2017/0308665 A1* | 10/2017 | Heck | A61M 5/14244 |

FOREIGN PATENT DOCUMENTS

| | | |
|---|---|---|
| EP | 2237483 A1 | 6/2010 |
| EP | 2237483 A1 | 10/2010 |
| EP | 2339559 A1 | 6/2011 |
| JP | 2001333068 A | 11/2011 |

OTHER PUBLICATIONS

European Examinational Report for Application No. 17718372.0, dated Mar. 30, 2020, 5 pages.
Office Action received in Chinese Patent Application No. 2017800280381, dated Jun. 24, 2020, 13 pages.
Office Action received in Chinese Patent Application No. 201780028038.1, dated Jan. 8, 2021, 8 pages.

\* cited by examiner

COMMUNICATIONS PROTOCOL FOR AN ELECTRONIC SYSTEM

CROSS-REFERENCE TO RELATED APPLICATIONS

This application is the 35 U.S.C. § 371 national stage of PCT/EP2017/059330, filed Apr. 20, 2017, which claims priority to British Patent Application No. 1607973.3, filed May 6, 2016, which are incorporated herein by reference in their entirety.

TECHNICAL FIELD

The present invention relates to a method of wireless communication between various electronic component devices of a system, such as a medical infusion system.

BACKGROUND

It is increasingly common for the components of domestic electronic systems to communicate with each other wirelessly. This can present problems for the designers of such systems.

For example, it is important that the communications between the components of the system are secure in that the component receiving the wireless communication knows that the communication originated from another component of the same system.

SUMMARY OF INVENTION

At its most general, the present invention proposes assigning a common system identification code to each of a control unit and a plurality of controllable slave units, storing that system identification code in a user-inaccessible memory of those units, and allowing pairing between the control unit and each of the slave units only if the system identification code of the control unit matches that of the respective slave unit.

According to a first aspect of the present invention, there is provided a system comprising: a control master unit, comprising a user-inaccessible memory storing a system identification code and a communication node for transmitting and receiving wireless signals; and a plurality of slave units, each slave unit comprising a user-inaccessible memory storing the system identification code, and a communication node for transmitting and receiving wireless signals. The control master unit is configured to transmit a control signal, the control signal comprising the system identification code; and each of the slave units is configured to receive the control signal, and act upon the control signal only in the event that the system identification code in the control signal matches the system identification code stored in the memory of the respective slave unit.

Thus a slave unit can only act upon a control signal if the control signal comes from the control master unit which shares the system identification code, i.e. is verifiably from the same family. This ensures that a slave unit only acts on instructions which come from a specified control unit, so providing security to the user. It is therefore impossible for a slave unit to act on instructions from any device other than the control master unit with which it shares a system identification code, which may be alternatively referred to as a family identification code or family ID.

The system may further comprise a second control unit having a user-inaccessible memory storing a second system identification code that is different to the system identification code, and a plurality of second slave units having a user-inaccessible memory storing the second system identification code, wherein the second control master unit is configured to transmit a second control signal, the control signal comprising the second system identification code. In such embodiments each of the second slave units is configured to receive the control signal, and act upon the control signal only in the event that the second system identification code in the control signal matches the second system identification code stored in the memory of the respective slave unit. Thus, the slave units of the first family defined by the system identification code cannot be controlled by the control unit of the second family defined by the second system identification code, and vice versa.

By user-inaccessible memory, it is meant that an end user of the device cannot access or modify the memory. That is, an unskilled person in device communications, or medical equipment, or another field relating to the invention, or a person who has not received specific training for programming such devices and is not authorised to do so. The end user is typically the purchaser of the device, and the person who utilises the device for its intended purpose. The end user is not a manufacturer of the device, a distributer of the device, a salesperson of the device or a medical practitioner providing the device.

The term slave device is used herein to refer to a device whose operation is controlled by a remote control unit. That is, a slave device is a device which carries out an operation in response to processing of a command instruction sent by a control device. The slave device will typically incorporate a drive member, actuating part or similar for carrying out that operation.

Each slave unit stores only a single system identification code. A slave unit can only pair with a single command master unit, ensuring that the actions performed by the slave unit originate from a single verified source.

The control signal may be configured to initiate pairing and establish a communications link between the control master unit and the one or more of the slave units. Once a connection between the slave unit and control master unit has been established, which is secure due to the verification of the system identity code, the slave unit and the control master unit can communicate freely.

The control master unit may be configured to pair with only a single slave unit at any one time. This provides certainty as to which slave unit is being controlled, and reduces unnecessary power output in pairing with a slave unit when it is not necessary to do so.

Each of the plurality of slave units may be configured to adopt a state of readiness to pair upon activation of the slave unit. This ensures that an activated slave unit is automatically available to pair with and receive instructions from a control master unit, providing an efficient, easy to operate system, and preventing any delay in pairing between a slave unit and control master unit.

Each of the slave units can be configured to adopt a state of unavailability for pairing once the communications link is established with the control master unit. This saves power in the slave unit and prevents unwanted additional pairing.

Because the system identification is stored at a user-inaccessible part of the memories of the control master unit and slave units, a user is prevented from modifying or otherwise compromising the system identification code which may be detrimental to the security of the system.

The system identification code is preferably encrypted within the memory of the control master unit and the respective memories of the plurality of slave units. This prevents an external source discovering the system identification code and using the code to establish a communications link with a slave unit.

The memory of the control master unit may further store a unique device identification code identifying the control master unit, and the memories of the plurality of slave units can further store unique device identification codes uniquely identifying the respective slave units. Device identification codes can be used to identify the pairing status of the control master unit and the slave units, and can be used to identify which units are paired at any given time.

The control master unit and the slave unit may pair with each other providing that the system identification code send in the initial polling massage from the control master unit to the slave unit contains the same system identification code as the system identification code stored within the slave unit. Thus two paired units (the control master unit and the slave unit) have the same system identification code. However, the two paired units will have different unique device identification codes. The device identification codes can be wirelessly communicated between the slave unit and the control master unit so that the control master unit can identify which device it is paired to. The identification of the paired units can then be relayed to the user, for example through a user interface on the control master unit.

Each slave unit within the system is programmed with a default slave unit name. The slave unit name is an identifying name which can be recognised by the end user, for example relating to a colour of the slave unit. Unlike the device identification code and the system identification code, the slave unit name can be stored in a part of the memory which can be accessed by the user. In this way, the user can change the slave unit name to something personal so that they can identify the slave units, whilst avoiding sharing the device identification code with the user which could compromise security in the system.

The control master unit can comprise a user interface, and the plurality of slave units preferably do not comprise a user interface. This allows for user input at the control master unit. As the control master unit can pair with a slave unit, the control master unit can send instructions corresponding to the user input to the slave unit, to control the slave unit. The slave unit does not have a user interface and so can be small, compact and light.

The system can be an infusion pump system, wherein the slave units can be pump units for infusing liquid into a patient. The slave unit could be a wearable device. The slave unit could be operable via the control master unit to pump a desired amount of therapeutic fluid into a patient. For example, the medical liquid could be insulin used to treat diabetes.

The system may be a medical system and the slave device is preferably a delivery device for delivering therapy to a patient. Processing the stored instruction comprises delivering therapy to a patient. Medical systems often employ wireless slave devices, particularly slave devices to be worn by a patient. In the medical field, it is essential that the correct therapy is delivered to a patient. An incorrect dose of therapy could be dangerous.

The medical system may be a fluid delivery system, and the delivery device may be a pumping device for pumping a therapeutic fluid wherein processing the stored instruction results in pumping the fluid into e.g. the subcutaneous tissue of a user. Fluid delivery is a field where wireless control of a delivery slave device, often a wearable delivery slave device, is desirable. Further, fluid delivered directly to a patient must be delivered in precise and correct dose. A delivery of too much or too little fluid could be dangerous.

The therapeutic fluid may be insulin. Insulin is delivered for the treatment of diabetes through a wearable insulin infusion system. Precise control over the volume and timing of fluid delivery is needed to control blood sugar levels in a diabetic. Any departure from the desired fluid delivery instructions could be dangerous to the user.

The communication node of the control master unit and the communication nodes of the slave units can be configured to transmit and receive wireless signals using a near-field wireless communications protocol, such as a BlueTooth® protocol. Using such communication protocol requires only a low level of power and so it not draining on the system's power resources. The communication node of the control master unit and/or slave units may comprise a transceiver or separate receiver and transponder, for example.

The communication nodes of the slave units can be capable of transmitting and receiving wireless signals only using the near-field wireless communications protocol, and wherein the communication node of the control master unit is capable of transmitting and receiving wireless signals using the near-field wireless communications protocol and at least one other wireless communications protocol. The at least one other wireless communications protocol may comprise an IEEE 802.11 communications protocol. This enables two-way patient support either directly or via an intermediate internet connected device such as a PC, laptop or mobile device.

A further aspect of the present invention provides a method in a system comprising a control master unit and a plurality of slave units, the control master unit comprising a user-inaccessible memory storing a system identification code and a communication node for transmitting and receiving wireless signals, each slave unit comprising a user-inaccessible memory storing the system identification code, and a communication node for transmitting and receiving wireless signals, the method comprising: by the control master unit, transmitting a control signal comprising the system identification code; and by one or more of the slave units, receiving the control signal, and acting upon the control signal only in the event that the system identification code in the control signal matches the system identification code stored in the memory of the one or more of the slave units.

Thus a slave unit can only act upon a control signal if the control signal comes from the control master unit which shares the system identification code. This ensures that a slave unit only acts on instructions which come from a verified source and provides security to the user. It is therefore impossible for a slave unit to act on instructions from any unit other than the control master unit with which it shares a system identification code, which may be referred to as a family identification.

As the system identification code is stored at a user-inaccessible part of the memories of the control master unit and the slave units, a user is prevented from determining the system identification code which may be detrimental to the security of the system.

The method may further include any of the features discussed above in relation to the system. In particular, the method may include the following additional features.

The method could further include, upon acting on the control signal, initiating pairing and establishing a communications link between the control master unit and the one or more of the slave units. Once a connection between the slave unit and control master unit has been established, which is secure due to the verification of the system identity code, the slave unit and the control master unit can communicate freely.

The control master unit may be configured to pair with only a single slave unit at any one time. This provides certainty as to which slave unit is being controlled, and reduces unnecessary power output in pairing with a slave unit when it is not necessary to do so.

Each of the plurality of slave units may be configured, upon activation, to adopt a state of readiness to pair. The method may include, after establishing a communications link with the control master unit, adopting a state of unavailability for pairing.

The system identification code may be encrypted within the memory of the control master unit and the memories of the plurality of slave units. This prevents an external source discovering the system identification code and using the code to establish a communications link with a slave unit.

The system identification code may be predefined by a manufacturer of the system. Again, this provides security for a user as the slave units can only be paired with a predetermined control master unit, such that a user can be confident no other control master unit is controlling a given slave unit.

The memory of the control master unit may store a unique device identification code identifying the control master unit, and the memories of the plurality of slave units may store unique device identification codes uniquely identifying the respective slave units. Device identification codes can be used to identify the status of the control master unit and the slave units, and can be used to identify which units are paired at any given time.

The control master unit may comprise a user interface, and the plurality of slave units may not comprise a user interface. This allows for user input at the control master unit. As the control master unit can pair with a slave unit, the control master unit can send instructions corresponding to the user input to the slave unit, to control the slave unit. The slave unit does not have a user interface and so can be small, compact and light.

The method may be a method of operating an infusion pump system, and the slave units may be pump units for infusing liquid into a patient. The slave unit could be a wearable device. The slave unit could be operable via the control master unit to pump a desired amount of therapeutic fluid into a patient. For example, the medical liquid could be insulin used to treat diabetes.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
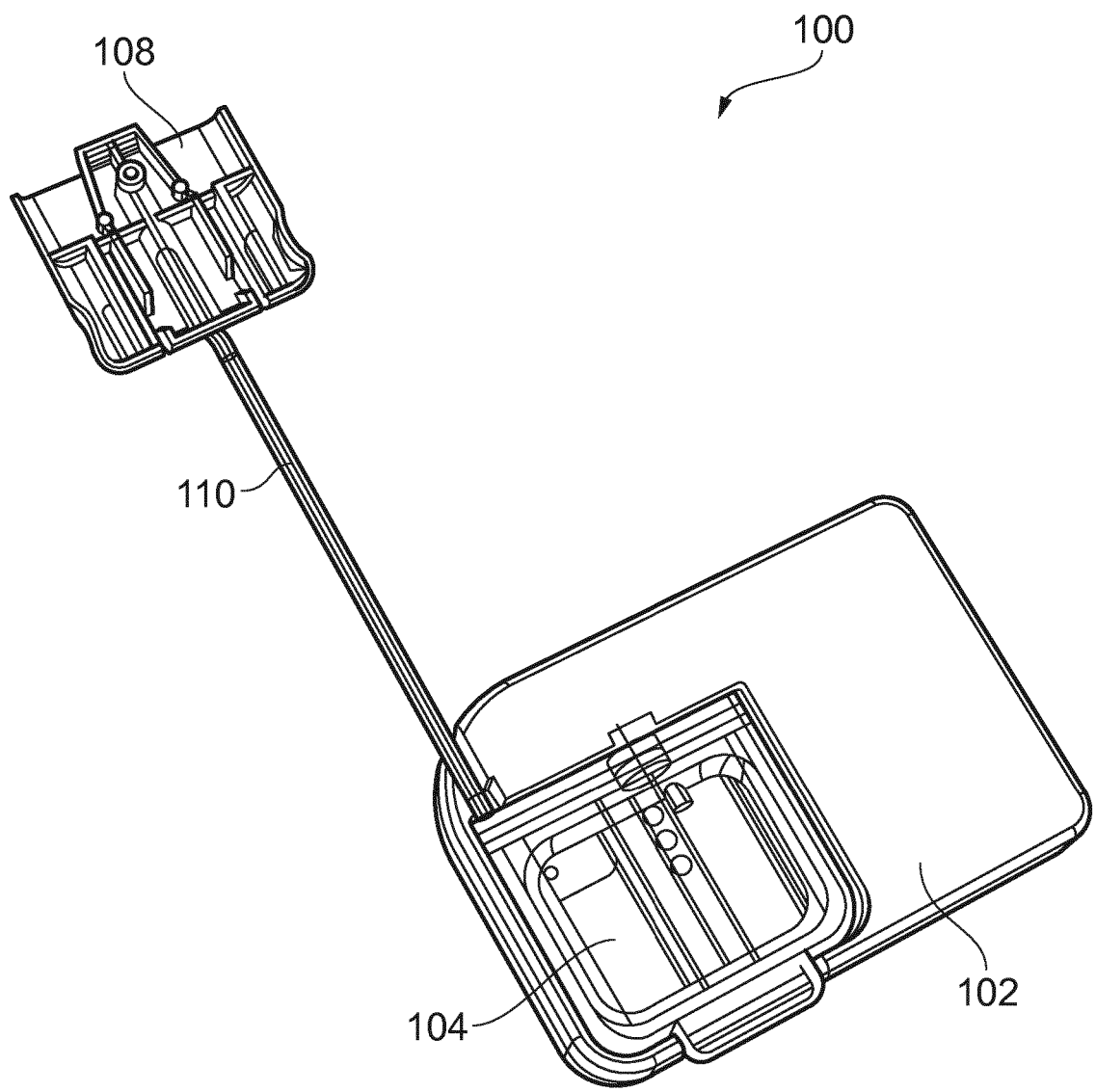
FIG. 1 shows a slave device for infusion of fluid to the human body.

FIG. 1 shows the wearable part of an external infusion system for the continuous subcutaneous infusion of insulin into the human body through repetitive small pulses of infusion. The infusion device 100 comprises a pump part 102, a replaceable cartridge 104 having an outlet port 106 connected to an infusion set 108 via an infusion tube 110. The infusion system forms a slave unit in the present invention.

Depending on the desired positioning of the pump part 102 with respect to the infusion set 108 during use, the length of the infusion tube 110 may be longer or shorter than that shown in FIG. 1, and indeed the infusion set 108 may be coupled directly to the output port 106 of the pump where close coupling of the infusion set 108 and the pump part 102 is desired, thereby avoiding the need for the flexible infusion tube 110.

The cartridge 104 includes a reservoir for storing a supply of insulin and a pumping chamber. The cartridge may be disposable and removably attached to a durable housing part of the infusion system. When the cartridge 104 is attached to the housing a drive member of the pump part 102 is operatively coupled to the pumping chamber for delivering a supply of insulin from the reservoir to the outlet port 106 and into the infusion set 108 via the infusion tube 110.

The infusion set includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula. Thus insulin is infused through the cannula into the human body.

It will be appreciated that any other kind of device in wireless communication with a control master unit can be used as a slave unit in accordance with the present invention, the delivery system of FIG. 1 is just one example. Other examples include, but are not limited to, a blood glucose monitor, a sub-cutaneous glucose monitor, an activity monitor, a heart rate monitor, a lactate threshold sensor, a biometric body sensor, an implantable device (such as a pace maker), or a smart pill.

Figure 2:
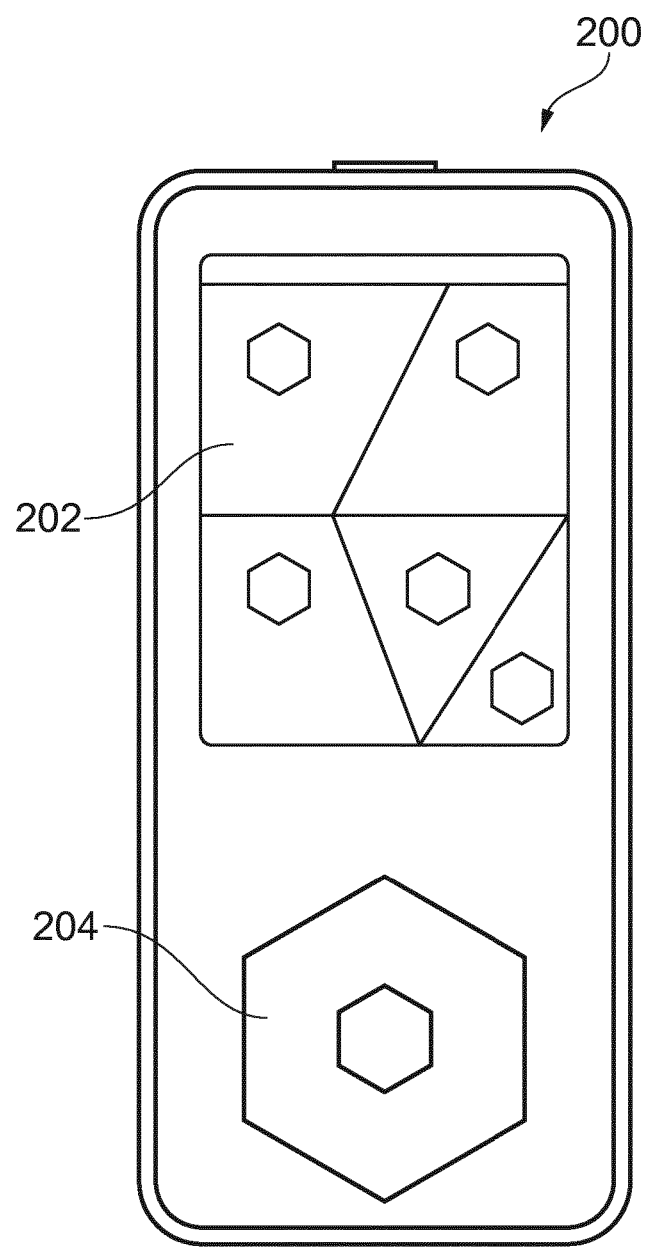
FIG. 2 shows a control master unit for controlling the slave device of FIG. 1.

FIG. 2 shows a control master unit 200 for wirelessly controlling the slave unit. The control master unit 200 includes a graphical user interface 202 and a tactile user interface 204.

The control master unit 200 can be used to instruct the device to pump insulin from the cartridge through the infusion system. The control master unit may instruct the volume of fluid to be delivered, the rate of delivery, the duration of delivery, start time, stop times, or any similar instruction to control the fluid delivery from the device.

The control master unit 200 further enables a user to perform the following functions:

Define and store basal profiles;
Transfer an active basal profile to the device 100;
Define and transmit a bolus request to the device 100;
Define and transmit a temporary basal to the device 100;
View a graphical representation of a bolus based on glucose readings from a separate blood glucose meter or entered manually following a blood glucose meter reading from a separate blood glucose meter (not shown);

View graphically pump performance over time;

Request the current status of the device 100 (including what insulin delivery is currently in progress, battery status, alarm conditions, insulin reservoir level, etc).

The reader will appreciate that the device must accurately perform the instructions which are sent by the control master unit. If the instruction processed by the device differs in any way from the instruction sent by the control master unit, the device may deliver an incorrect volume of fluid. In the field of insulin delivery, this may be dangerous.

Figure 3:
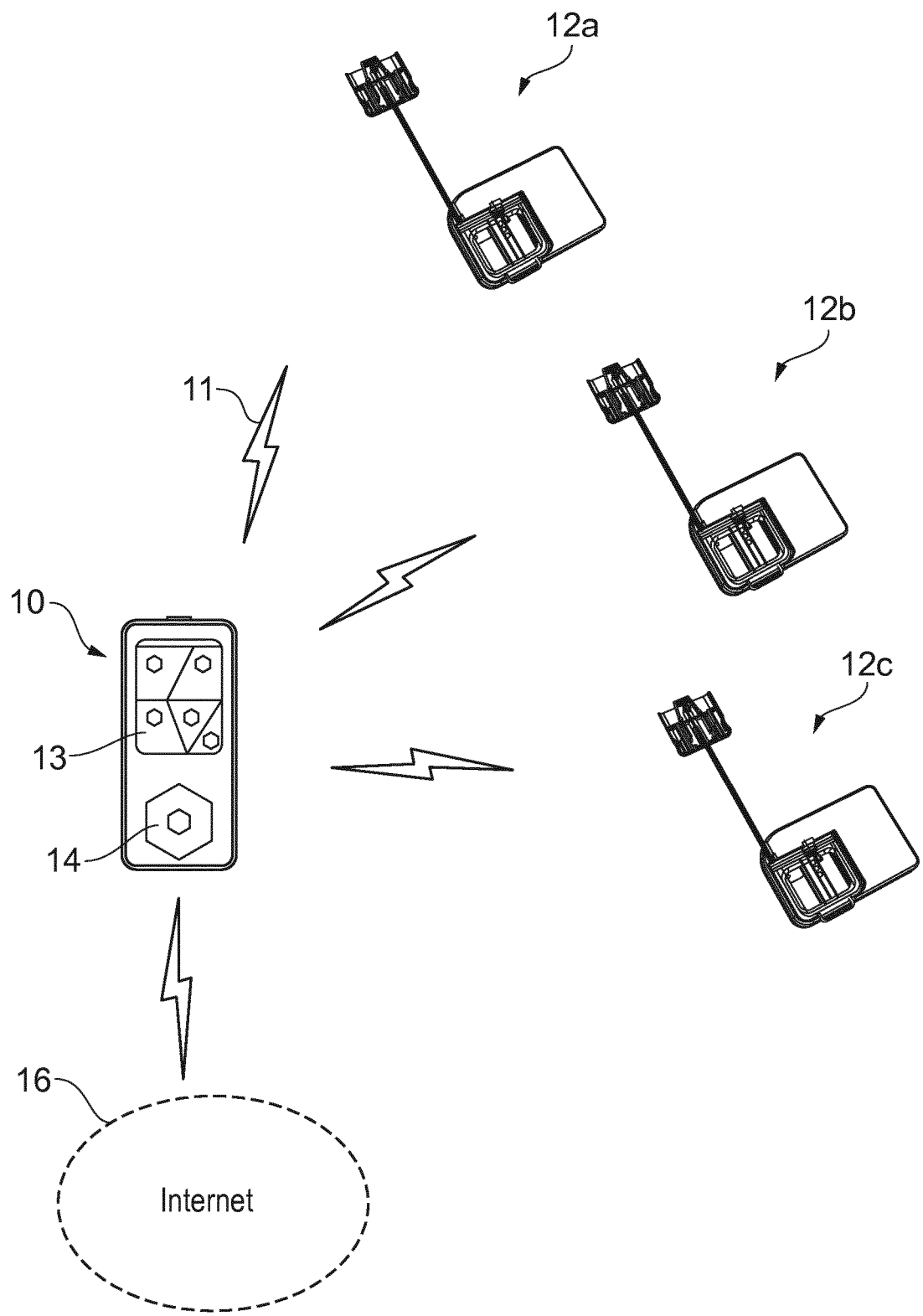
FIG. 3 shows an electronic system according to embodiments of the invention.

FIG. 3 shows an electronic system according to aspects of the present invention. The system comprises a family of units including: a control master unit 10, and multiple slave units 12*a*, 12*b* and 12*c*. Any number of slave units could be included in a single family.

The control master unit can communicate wirelessly with each slave unit as indicated by jagged arrows 11. The wireless communication may be via Bluetooth™ or other radio frequency near field communication means.

The control master unit 10 can also connect to the internet 16, and as such is Bluetooth™ or Wi-Fi enabled for internet connectivity. The internet connectivity enables two-way patient support either directly or via an intermediate internet connected device such as a PC, laptop or mobile device.

The electronic system may be an infusion pump system, where the slave units are pump units for infusing a liquid into a patient.

In this embodiment, each slave unit 12*a*, 12*b* and 12*c* is a wearable part of an external infusion system for the continuous subcutaneous infusion of fluid into the human body through repetitive small pulses of infusion. The slave units can store fluid, for example, in a removable cartridge 104. The fluid may be therapeutic fluid, for example insulin. Each slave unit includes a pump (not shown) for pumping the fluid and infusing it into a patient.

The control master unit 10 includes a graphical user interface 13 and a tactile user interface 14.

The control master unit 10 can be used to instruct the slave units 12 to infuse liquid into a patient. The control master unit 10 may instruct the volume of fluid to be delivered, the rate of delivery, the duration of delivery, start time, stop times, or any similar instruction to control the fluid delivery from the device.

When a user is using a slave unit (for example slave unit 12*a*) the control master unit 10 will be used to control that unit. The other slave units will not be in use and will be, for example, in a hibernation mode or recharging mode where they do not communicate with the control master unit.

After a period of time in use, the slave unit 12*a* will need replacing. A slave unit may be worn for a period of time before it needs replacing. A slave unit may need replacing, for example, if the slave unit runs out of power.

The slave unit 12*a* is removed from the body and replaced with another slave unit from the family (for example slave unit 12*b*). The control master unit 10 then ceases to control the slave unit 12*a* and instead controls the slave unit 12*b*.

The control master unit 10 and each of the slave units 12*a*, 12*b*, store in their respective memories a system identification code, which may alternatively be referred to as the family ID code. The system identification code is unique to the system. That is, the system identification code identifies the slave units which are controllable by (i.e. belong in the same family as) a particular control unit. The system identification code is pre-programmed into the respective memories of the control unit and controllable slave units before the products are received by the end user, for example by the manufacturer, retailer or a healthcare professional. Further, the system identification code is programmed into the products in non-volatile memory. The devices are therefore pre-programmed with the system identification code before being received by the end user. Moreover, the system identification code is inaccessible by the end user. That is, the end user cannot change or otherwise influence the system identification code stored by the control master unit 10 or slave units 12*a*, 12*b* etc.

The control master unit 10 and each slave unit 12 also have stored in their respective memories a unique device identification code. That is, the control unit 10 stores a unique control master unit device identification code which uniquely identifies that control master unit 10, and each slave unit 12 stores a unique slave unit identification code that uniquely identifies that slave unit. Thus, a first slave unit identification code corresponds to the first slave unit 12*a*, a second slave unit identification code corresponds to the second slave unit 12*b*, and so on. Like the system identification code, the unique device identification codes are also stored in the memories of the respective devices before the system is received by the end user, and are inaccessible by the user. The unique device identification codes are programed into non-volatile user-inaccessible memory. The devices are therefore pre-programmed with their respective device identification codes before being received by the end user. In some embodiments the device identification codes may be inaccessible by the end user. That is, the end user cannot change or otherwise influence the unique device identification codes stored by the control master unit 10 or slave units 12*a*, 12*b* etc.

Each slave unit within the system is programmed with a slave unit name. The slave unit name is an identifying name which can be recognised by the end user. For example, each slave unit may include a visible surface marker of a different colour, and the default slave unit name may be related to the colour of the slave unit. Unlike the device identification code and the system identification code, the slave unit name can be stored in a part of the memory which can be accessed by the user. In this way, the user can change the slave unit name to something personal so that they can identify the slave units, whilst avoiding sharing the device identification code or family identification code with the user, which could compromise security in the system.

Each slave unit 12 in a family is used by a single user, and the user can only use one slave unit at a time. Therefore the control master unit 10 is only required to control a single slave unit at any one time.

Each slave unit should only be capable of implementing instructions received from the corresponding control master unit. Acting on instructions received from another, external, source, may have dangerous consequences. An external source may attempt to hack the system through communicating with the slave units 12*a*, 12*b* and 12*c*. If the slave units act upon control instructions from an external source, an incorrect instruction may be performed which could lead to a major health issue. For example, a slave unit may deliver too much or too little therapeutic fluid, which may be severely dangerous to the health of the user.

Thus the connections between the slave units and the control master unit must be secure from hacking so that the only instructions implemented by the slave units originate from the control master unit. To ensure that the message processed by the slave unit was received from the corresponding control master unit, embodiments of the system include a system identification code included within the wireless instructions. The slave unit must confirm that the system identification code is correct before processing the instruction. These embodiments are described in more detail below.

Figure 4:
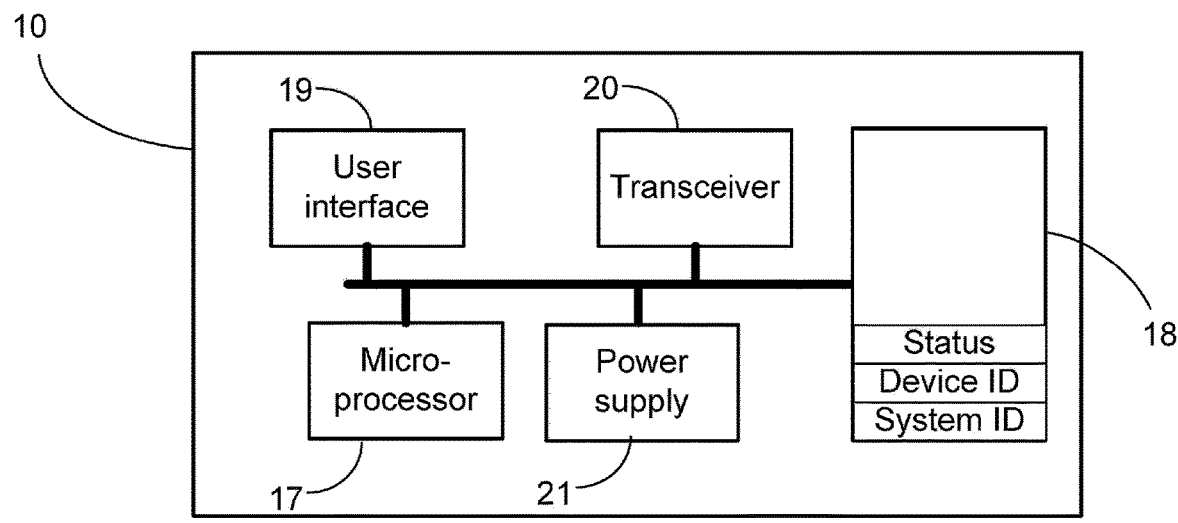
FIG. 4 shows in schematic detail a control master unit of the electronic system according to embodiments of the invention.

FIG. 4 shows a schematic representation of the control master unit 10. The control master unit 10 includes a communication node 20 for wireless communication with the slave units 12. The wireless communication may be via Bluetooth™ or other radio frequency near field communication means. The communication node 20 also can connect wirelessly to the internet.

The control master unit includes a user interface 19, which may include a tactile user interface for user input. The control master unit further includes a micro-processor 17 for processing instructions received via the communication node 20 or via the user interface 19. The control master unit 10 includes a power supply 21 for powering the control master unit. The power supply 21 may be a battery, and in an embodiment the battery is rechargeable.

The control master unit 10 includes a memory 18 which stores a device identification which is unique to the control master unit, and a system identification which is unique to the system (i.e. family) of control master unit 10 and controllable slave devices 12. The memory also stores the status of the control master unit.

Figure 5:
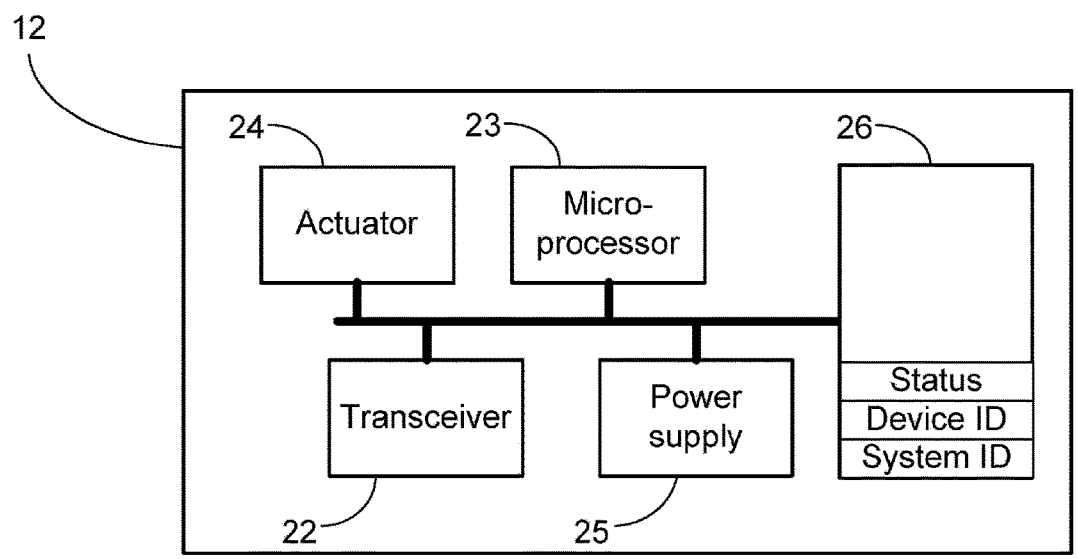
FIG. 5 shows in schematic detail a slave device of the electronic system according to embodiments of the invention.

FIG. 5 shows a schematic representation of a slave unit 12. The slave unit includes a communication node 22 for wireless communication with the control master unit 10. The wireless communication may be via Bluetooth™ or other radio frequency near field communication means. The slave unit does not have means for any other other wireless communication.

A single near-field communication protocol requires only a small amount of power, and the slave unit can be small and compact. Because the unit con only communicative wirelessly using a single protocol, this enhances the unit's security and reduces the possibility of hacking.

The slave unit 12 further includes a micro-processor 23 for processing instructions. Also included in the slave unit is an actuator 24 (actuating part, or drive member), for, in this embodiment, pumping fluid from the unit. The actuator responds to instructions processed by the microprocessor. The slave unit does not include a user interface. This allows for a smaller and more compact slave unit which is suited to being a wearable device.

The slave unit further includes a memory 26. The memory stores a device identification code which is unique to each individual slave unit, as discussed above. The memory also stores the system identification code which is unique to the system (i.e. family) of control master unit 10 and controllable slave devices 12. The memory also stores the status of the slave unit.

The features shown in FIGS. 4 and 5 are those relevant to the present invention, and the skilled person will understand that the control master unit and slave units may include further elements.

Figure 6:
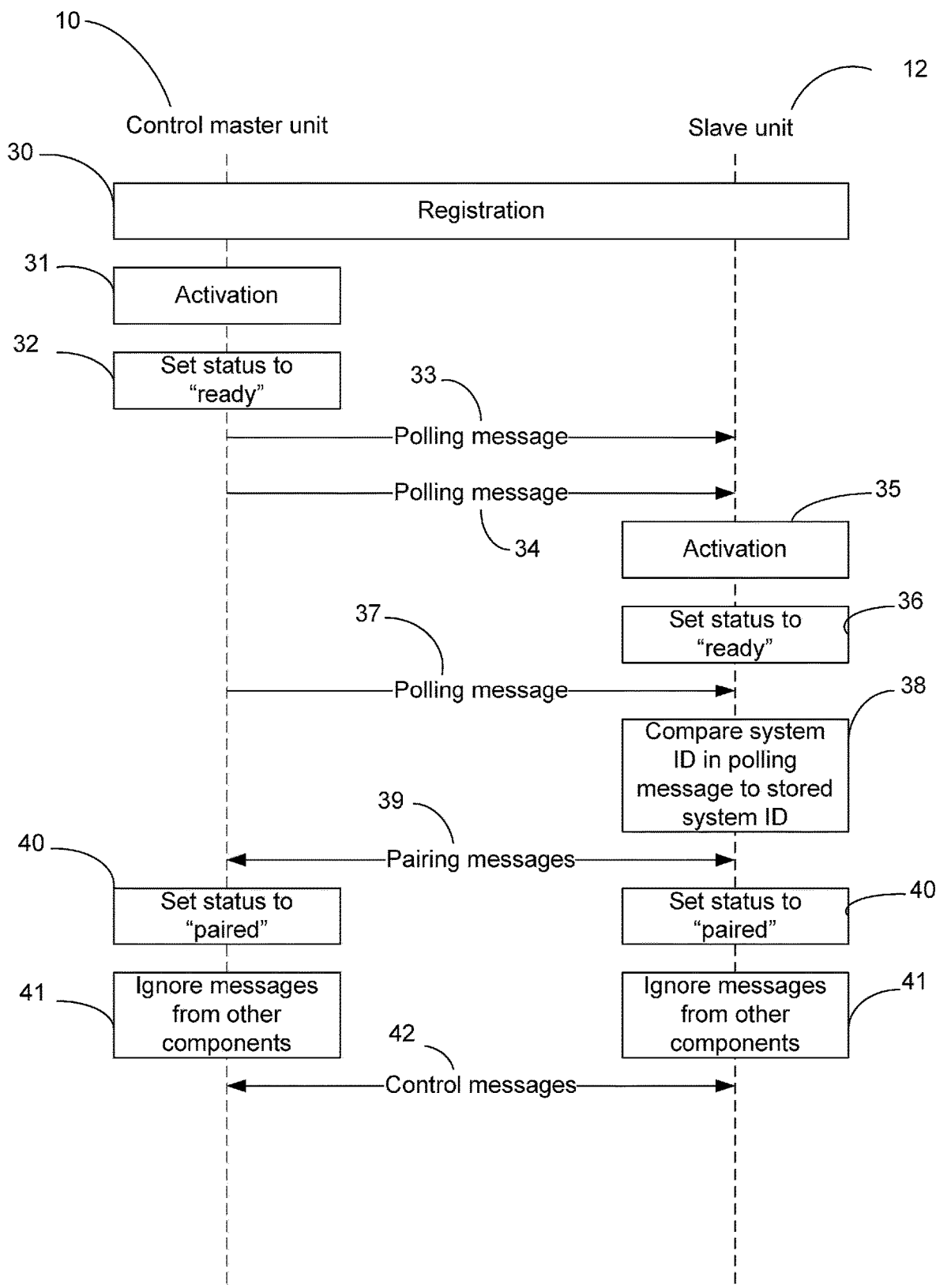
FIG. 6 is a signalling diagram showing a method according to embodiments of the invention.

FIG. 6 shows a signalling diagram of a method according to the present invention. The vertical dashed rails indicate signals sent to and from the control master unit (on the left) and the slave unit (on the right). Horizontal arrows between the two dashed rails indicate signals being sent between the control master unit 10 and the slave unit 12. The direction of the arrowhead indicates the direction of travel of the signal.

The process begins at Registration 30. In registration, the suite of products in the system, i.e. the control master unit and each of the controllable slave units which together make up the family of units, is programmed with the system identification code. The system identification code is unique to the system. The system identification code is pre-programmed into the suite of products before the products are received by the end user. Further, the system identification code is programmed into the products in non-volatile memory. The devices are therefore pre-programmed before being received by the user.

The system identification code is programmed into the control master unit using a USB port within the control master unit, or wirelessly. The slave unit has no physical contact point and the system identification code is programmed into the slave unit memory using wireless communication. The system identification code is preferably set in the control master unit and its respective controllable slave units at the same time. This can be done by the manufacturer, by a product distributor, or by a healthcare professional issuing the system to a patent.

Further, during registration a unique device identification code is programmed into each unit of the system. The device identification codes are used to identify each of the control master unit and the slave units within the system. There is, for example, a control master unit device identification code, a first slave unit identification code corresponding to a first slave unit, a second slave unit identification code corresponding to a second slave unit, and so on. The unique device identification codes are programmed before the system is received by the end user. The unique device identification codes are programed into non-volatile user-inaccessible memory.

Each slave unit within the system is programmed with a slave unit name. The slave unit name is an identifying name which can be recognised by the end user. For example, each slave unit include a visible surface marker of a different colour, and the default slave unit name is related to the colour of the slave unit. Unlike the device identification code and the system identification code, the slave unit name can be stored in a part of the memory which can be accessed by the user. In this way, the user can change the slave unit name to something personal so that they can identify the slave units, whilst avoiding sharing the device identification code or system identification code with the user, which could compromise security in the system.

As discussed above, the step Registration 30 is performed before the system is received by the end user. The subsequent steps are performed once the system has been received by the end user.

Next the control master unit 10 activates at 31. This may be in response to the control master unit being powered on by a user. Once the control master unit is activated, the pairing status of the control unit is set to "ready" at step 32. When the control master unit is in the "ready" state, it is in a state of readiness for pairing with a slave unit.

To attempt to pair with a slave unit the control master unit wirelessly transmits a polling message 33 using near field communication means. The polling message is configured to initiate pairings and establish communication with a slave unit.

In order to be able to pair with the control unit, the slave unit 12 must first be activated, and in a "ready" state. Before activation the slave unit is not available for pairing or establishing communication. In the example process illustrated in FIG. 6 the slave unit is not activated when polling message 33 is sent, and the control master unit 10 therefore remains in a "ready" state.

If the polling message 33 is not received, then the control master unit 10 will transmit a further polling message 34.

Polling messages may be transmitted at regular intervals for the duration the time the control master unit spends in a "ready" state. Polling message 34 is not received by the slave unit as the slave unit is still not in a "ready" state.

At step 35 the slave unit is activated. In other embodiment activation of the slave unit may occur at an earlier stage, and in particular before activation of the control master unit at step 31. Activation of the slave unit may be achieved by the user powering on the slave unit. The slave unit may automatically be powered on, and hence activated, upon the insertion of a cartridge of fluid into the slave unit.

Typically the user will power on the slave unit as soon as they start wearing the unit for the infusion of fluid into the body. Once the slave unit is activated the slave unit pairing status is automatically set to "ready" at step 36. When the slave unit is in the "ready" state the slave unit is available for pairing and for establishing communication. The slave unit is configured to, when in the "ready" state, search for a control master unit with which to pair. The slave unit may actively search for a pairing or may passively search (i.e. may be available for the control master unit to pair with).

As the control master unit received no response to polling message 34, it transmits another polling message 37. At this time the slave unit has been activated and is in a "ready" state. Therefore the slave unit can receive the polling message 37.

The polling message includes a request to initiate pairing between the control master unit 10 and the slave unit 12, and further includes the system identification code.

Upon receiving the polling message 37, the slave unit, at step 38, compares the system identification code included in the polling message with the system identification code stored in the slave unit memory.

If the system identification codes do not match then the slave unit will not process the polling message and pairing will not be initiated. The control master unit 10 will therefore continue to transmit polling messages and to have the pairing status "ready".

Only if the system identification code included in the polling message with the system identification code stored in the slave unit memory match will the slave unit processes the polling message. Processing the polling message initiates pairing between the slave unit and the control master unit.

Pairing messages 39 are then sent between the slave unit and the control master unit.

The pairing message from the slave unit to the control master unit may include the slave unit's device identification code. This allows for identification of the units which are present in the pairing.

The control master unit could display the pairing status on the user interface of the control master unit. This could include displaying details of the slave unit with which is it paired. For example, the control master unit can display the user-programmable slave unit name corresponding to the unique device identification code of the slave unit. The slave unit name can be chosen by the user so that the user instantly recognises the slave unit in use. Further, the control master unit does not need to display the unique device identification code of the slave unit, thus further enhancing security.

It is not necessary for the control master unit to send its unique device identification code to the slave unit, since the slave unit has no display interface for displaying this information to the user. The slave unit is aware that it is connected to a verified control master unit through the system identification code contained within the initial polling massage from the control master unit. However, in some circumstances it may be desirable that the control master unit sends its unique device identification code to the slave unit.

The pairing messages 39 trigger both the control master unit and the save unit to set their pairing status to "paired" at step 40. When the control master unit has a status of "paired" it ceases to transmit any further polling messages (until the status returns to "ready" at some point in the future). Further, when the status is "paired" the control master unit will ignore any messages from other slave units at 41. Thus the control master unit can only be paired with a single slave unit at one time. Likewise, when the status of the slave unit is "paired" it will ignore messages from other control master units so can only be paired with a single control master unit at any one time.

Once the control master unit and the slave are paired, control messages 42 are sent wirelessly between the two. The control messages include instructions from the control master unit to the slave unit so that the control master unit can control operation of the pump of the slave unit. Thus the slave unit and the control master unit are in communication with one another.

The above process ensures that an external source cannot control a slave unit. The slave unit only receives polling messages when in the "ready" state. If, when in the "ready" state, the slave unit receives a polling message from an external source, the slave unit will compare any system identification code in the polling message to the system identification code stored in the memory of the slave unit. A polling message received from an external source will either not have a system identification code, or will contain a different system identification code. Thus when the slave unit compares the two identification codes (at step 38), it will establish that the two codes do not match and therefore it will not act upon the polling message, therefore the slave unit will not be paired with the external source. This removes the danger of the slave unit being controlled by any other unit than the control master unit within the family.

If the two codes do not match and the slave unit does not pair with the external source, then the slave unit will maintain a status of "ready" and will be available for pairing with the control master unit from its family, i.e. the single control master unit which carries the same system identification code as the slave unit.

If an external source could determine the system identification code, then a message originating from the external source, but appearing to originating from the control master unit could be sent. Therefore to further secure this system the system identification code can be encrypted when stored in the memory of the control master unit and/or the memory of the slave units. An encrypted system identification code prevents a hacker from breaking into the units and discovering the system identification code, which ensures that the system identification code contained within a message can be guaranteed to originate from the control master unit.

Additionally the system identification code is stored in an area of the control master unit and slave unit memory which is not accessible to the user. The system identification code is stored in the memory before the system is supplied to the user (e.g. during manufacture, by a retailer or a medical professional) and cannot be edited at a later date. The user cannot adjust a slave unit to communicate with a different family. The system is purchased by the user as a predetermined set, with each slave device and the control master unit in that set sharing a single system identification code. Any unit within that family will automatically only communicate with the corresponding unit or units within the same family.

This prevents a situation when a control master unit is inadvertently being used to control an incorrect slave unit, e.g. a slave unit of another user.

Further this increases ease of use of the system. The slave units do not include a user interface, so the user can activate a unit and trust that it will pair correctly with the control master unit without any further user input. The user can be sure that no external source will be able to control the pump of the slave unit, and that the control master unit is being used to control the correct slave unit, i.e. the slave unit that is currently activated. The system eliminates the need for the user to input information concerning which slave unit is currently being used, and to manually initiate pairing. The user only needs to activate the slave unit, and the pairing and later control signalling is performed automatically by the system.

A system is provided with a control master unit and a plurality of slave units which are all pre-programed to share a system identification code. The system identification code cannot be accessed or modified by the end user, which provides security to the system. A slave unit will only process an instruction from a control master unit with a matching system identification code. Further, the control master unit and each slave unit in the system is uniquely identifiable by a pre-programmed unique device identification code.

Thus there is provided an electronic system comprising a family of a control master unit and multiple slave units, wherein the control master unit can communicate with each of the slave units. The slave units are configured to only pair with the control master unit from the same family, and thus the system is secure from hacking by an external source.

Those skilled in the art will appreciate that various amendments and alterations can be made to the embodiments described above without departing from the scope of the invention as defined in the claims appended hereto.

The invention claimed is:

1. A medical system comprising:
   a control master unit, comprising a communication node for transmitting and receiving wireless signals and a user-inaccessible memory storing a system identification code; and
   a plurality of slave units, each slave unit being a delivery device having a pump for delivering therapy to a patient, each slave unit comprising a communication node for transmitting and receiving wireless signals and a user-inaccessible memory storing the system identification code;
   wherein the control master unit is configured to transmit a control signal and a control message, the control signal comprising the system identification code and being configured to initiate pairing and establish a communications link between the control master unit and the respective slave unit; and
   wherein each of the slave units is configured to receive the control signal, and pair and establish the communications link with the control master unit only in the event that the system identification code in the control signal matches the system identification code stored in the memory of the respective slave unit, and wherein each of slave units controls operation of the pump upon receiving the control message from the control master unit.

2. The medical system according to claim 1, wherein the control master unit is configured to pair with only one of the plurality of slave units at any one time.

3. The medical system according to claim 1, wherein each of the plurality of slave units is configured to adopt a state of readiness to pair upon activation.

4. The medical system according to claim 3, wherein each of the slave units is configured to adopt a state of unavailability for pairing once the communications link is established with the control master unit.

5. The medical system according to claim 1, wherein the system identification code is encrypted within the memory of the control master unit and the respective memories of the plurality of slave units.

6. The medical system according to claim 1, wherein the system identification code is predefined by a supplier of the system to an end user.

7. The medical system according to claim 1, wherein the memory of the control master unit stores a unique device identification code identifying the control master unit, and wherein the memories of the plurality of slave units each store unique device identification codes uniquely identifying the respective slave units.

8. The medical system according to claim 1, wherein the control master unit comprises a user interface, and wherein the plurality of slave units do not comprise a user interface.

9. The medical system according to claim 1, wherein the medical system is a fluid delivery system for pumping a therapeutic fluid.

10. The medical system according to claim 9, wherein the therapeutic fluid is insulin.

11. The medical system according to claim 9, wherein controlling operation of the pump comprises pumping a desired amount of therapeutic fluid into a patient.

12. The medical system according to claim 1, wherein the communication node of the control master unit and the communication nodes of the slave units are configured to transmit and receive wireless signals using a near-field wireless communications protocol.

13. The medical system according to claim 12, wherein the communication nodes of the slave units are capable of transmitting and receiving wireless signals only using the near-field wireless communications protocol, and wherein the communication node of the control master unit is capable of transmitting and receiving wireless signals using the near-field wireless communications protocol and at least one other wireless communications protocol.

14. The medical system according to claim 1, wherein the system identification code is unique to each slave unit.

15. The medical system according to claim 1, wherein the system identification code is pre-programmed into the control master unit memory and the each slave unit memory before the control master unit and slave unit are received by an end user.

16. The medical system according to claim 1, wherein the system identification code in the control master unit memory and the system identification code in the slave unit memory cannot be changed by an end user.

17. A method in a medical system comprising a control master unit and a plurality of slave units, the control master unit comprising a communication node for transmitting and receiving wireless signals and a user-inaccessible memory storing a system identification code, each slave unit being a delivery device having a pump for delivering therapy to a patient, each slave unit comprising a communication node for transmitting and receiving wireless signals and a user-inaccessible memory storing the system identification code, the method comprising:
   by the control master unit, transmitting a control signal and a control message, the control signal comprising the system identification code and being configured to initiate pairing and establish a communications link between the control master unit and the respective slave unit; and by one or more of the slave units, receiving the control signal, and pair and establish the communications link with the control master unit only in the event that the system identification code in the control signal matches the system identification code stored in the memory of the one or more of the slave units, and, upon receiving the control message from the control master unit, control operation of the pump.

\* \* \* \* \*